United States Patent
Kravitz et al.

(10) Patent No.: US 11,083,682 B2
(45) Date of Patent: Aug. 10, 2021

(54) COMPOSITION AND METHOD FOR IMPROVING AND PROTECTING KERATINS

(71) Applicant: Marianna Industries, Omaha, NE (US)

(72) Inventors: Joseph I. Kravitz, Omaha, NE (US);
Sara M. Dreamer, Omaha, NE (US);
Angelia J. Francis, Omaha, NE (US);
Steve M. Hudson, Omaha, NE (US);
Thomas D. Boatright, Council Bluffs, IA (US)

( * ) Notice: Subject to any disclaimer, the term of this patent is extended or adjusted under 35 U.S.C. 154(b) by 0 days.

(21) Appl. No.: 16/048,432

(22) Filed: Jul. 30, 2018

(65) Prior Publication Data

US 2018/0333343 A1 Nov. 22, 2018

Related U.S. Application Data

(62) Division of application No. 15/282,956, filed on Sep. 30, 2016, now abandoned.

(60) Provisional application No. 62/284,449, filed on Sep. 30, 2015.

(51) Int. Cl.
| | |
|---|---|
| *A61K 8/60* | (2006.01) |
| *A61Q 5/08* | (2006.01) |
| *A61K 8/86* | (2006.01) |
| *A61Q 5/04* | (2006.01) |
| *A61Q 5/00* | (2006.01) |
| *A61Q 5/10* | (2006.01) |

(52) U.S. Cl.
CPC ............... *A61K 8/602* (2013.01); *A61K 8/86* (2013.01); *A61Q 5/002* (2013.01); *A61Q 5/04* (2013.01); *A61Q 5/08* (2013.01); *A61Q 5/10* (2013.01); *A61K 2800/591* (2013.01); *A61K 2800/884* (2013.01)

(58) Field of Classification Search
CPC .... A61K 8/602; A61K 8/86; A61K 2800/591; A61K 2800/884; A61Q 5/10; A61Q 5/002; A61Q 5/04; A61Q 5/08
See application file for complete search history.

(56) References Cited

U.S. PATENT DOCUMENTS

| | | | |
|---|---|---|---|
| 3,676,550 A * | 7/1972 | Anzuino | A61Q 5/00 424/70.4 |
| 6,939,537 B2 | 9/2005 | Ohta | |
| 9,089,500 B2 | 7/2015 | Dublanchet et al. | |
| 2002/0155962 A1* | 10/2002 | Cincotta | A61K 8/8182 510/119 |
| 2007/0264208 A1 | 11/2007 | Mougin et al. | |
| 2010/0278764 A1 | 11/2010 | Mougin et al. | |
| 2012/0027698 A9 | 2/2012 | Mougin et al. | |
| 2014/0155352 A1 | 6/2014 | Dublanchet et al. | |
| 2014/0196740 A1* | 7/2014 | Mette | A61K 8/37 132/202 |
| 2015/0034117 A1 | 2/2015 | Pressly et al. | |
| 2015/0034119 A1 | 2/2015 | Pressly et al. | |
| 2015/0037270 A1 | 2/2015 | Pressly et al. | |
| 2015/0037271 A1 | 2/2015 | Pressly et al. | |
| 2015/0328101 A1 | 2/2015 | Pressly et al. | |
| 2015/0290101 A1 | 10/2015 | Pressly et al. | |
| 2015/0328102 A1 | 11/2015 | Pressly et al. | |
| 2016/0051458 A1 | 2/2016 | Dublanchet et al. | |
| 2016/0193129 A1 | 7/2016 | Pressly et al. | |
| 2016/0206535 A1 | 7/2016 | Pressly et al. | |
| 2016/0263003 A1 | 9/2016 | Pressly et al. | |

* cited by examiner

*Primary Examiner* — Matthew P Coughlin
*Assistant Examiner* — Thurman Wheeler
(74) *Attorney, Agent, or Firm* — Luke Charles Holst; McGrath North Mullin & Kratz, PC LLO

(57) ABSTRACT

The present invention relates in general to keratin treatment compositions and methods, and more specifically, compositions comprising up to 60% olefinic compounds and at least one unactivated double bond, the composition comprising fatty acid esters of polyhydric alcohols. The present invention is configured to be easily incorporated into bleaching processes, coloring processes, perming processes, shampoos, conditioners and/or styling products. The purpose of the invention is to provide a composition and method that will improve the overall health of keratins, in particular, texture, body, shine and strength.

18 Claims, No Drawings

COMPOSITION AND METHOD FOR IMPROVING AND PROTECTING KERATINS

CROSS REFERENCE TO RELATED APPLICATIONS

This application is a divisional of application Ser. No. 15/282,956, filed Sep. 30, 2016, which claims priority under 35 U.S.C. § 119 to provisional application Ser. No. 62/284,449, filed Sep. 30, 2015, herein incorporated by reference in their entirety.

FIELD OF THE INVENTION

The present invention relates in general to keratin treatment compositions and methods, and more specifically, compositions comprising up to 60% olefinic compounds with at least one unactivated double bond. The purpose of the invention is to provide a composition and method that will improve the overall health of keratins, in particular, texture, body, shine and strength.

BACKGROUND OF THE INVENTION

Keratins are a collective name for a group of proteins forming the main structural component in hair, nails, skin, hooves, claws, feathers and horns. These proteins comprise long chains of amino acids bound together via disulfide bonds, hydrogen bonds and salt bridges. A disulfide bond is a covalent bond derived from two thiol groups. Over time and stress the disulfide bonds may become broken, leaving keratins dry, unmanageable, dull and unhealthy. Treatment of keratins, such as in hair, have traditionally involved the application of conditioning agents that deposit hydrophobic or silicone-based compounds on the surface to improve softness, manageability and shine. Traditional conditioning agents are not chemically bonded to the hair, consequently, their effects are temporary and often last only until the next shampoo.

To solve the need for a more durable and long-lasting effect, a variety of approaches have been developed that utilize hydrophobic conditioning compounds with groups reactive toward thiols. These conditioning compounds attach the hydrophobic group onto the keratin through silanetriol functionality. Another approach binds two or more thiol-reactive groups onto the same hydrophobic conditioning compound. In this manner, native disulfide bonds that would normally connect two thiol groups on the keratin are replaced with a tethered structure to strengthen and repair damaged keratin through a network of covalent bonds. However, this approach suffers from inefficiency because the two reactive thiol groups on the same hydrophobic conditioning compound may react with one another to form an internal disulfide bond. The resulting cyclic molecule which once contained the two tethered thiol groups is therefore unreactive toward thiol groups on the keratin structure.

Still yet another approach involves the use of maleic acid as a thiol-reactive moiety. Being an α, β-unsaturated carboxyl compound, maleic acid readily undergoes a thiol-ene reaction whereby the thiol group adds across the double bond through a nucleophilic reaction mechanism known as a Michael Addition. Activation of the double bond in the maleic acid moiety toward nucleophilic addition is due to it being conjugated to an electron withdrawing carboxy group. Compounds possessing double bonds conjugated to electron withdrawing such as carbonyl or carboxy groups are known as Michael acceptors. In other words, the α, β-unsaturated compound undergoing Michael Addition is called the Michael acceptor. Thus, a conditioning agent/molecule having at least two Michael acceptors tethered through a network of covalent and ionic bonds has been utilized for improved and more durable keratin conditioning effects. In particular, the conditioning agent/molecule comprises bis-(aminopropyl)diethyleneglycol dimaleate having the chemical structure:

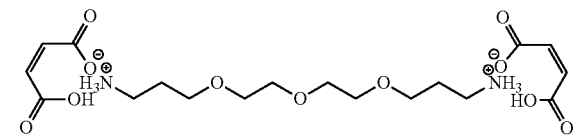 [SMILES: O=C([O-])/C=C\C(=O)O ; [NH3+]CCCOCCOCCOCCC[NH3+] ; O=C([O-])/C=C\C(=O)O]

The two maleic acid groups are tethered through diethylene glycol, with the hydroxyl group on each end being capped with an aminopropyl group. Notably, each primary amine function on the ends of bis-(aminopropyl)diethyleneglycol dimaleate is ionically bonded to a molecule of maleic acid through a proton transfer known as a salt bridge. Incorporation of ionic bonds, along with covalent bonds, weakens the tether between the multiple thiol-reactive groups. Thus, the salt bridges in this approach are susceptible to water and other ionic materials employed in the shampoo process, causing them to break, leading to reduced and shorter-lived keratin conditioning benefits.

For these reasons, a desire remains to further develop compositions and methods for improving and protecting keratins that overcome the aforementioned problems and improve the overall health of keratins with long-lasting and durable effects.

BRIEF SUMMARY OF THE INVENTION

Therefore, it is a principal object, feature, and/or advantage of the present invention to overcome the aforementioned deficiencies in the art and provide a composition and method of treating keratins that improve the overall health of keratins including texture, body, shine and strength.

A further object, feature, and/or advantage of the present invention is to provide a composition and method of treating keratins that produces long-lasting and durable effects.

Another object, feature, and/or advantage of the present invention is to provide a composition and method of treating keratins that can be easily incorporated into a keratin bleaching process.

Yet another object, feature, and/or advantage of the present invention is to provide a composition and method of treating keratins that can be easily incorporated into a keratin coloring process.

A still further object, feature, and/or advantage of the present invention is to provide a composition and method of treating keratins that can be easily incorporated into a keratin perming process.

Another object, feature, and/or advantage of the present invention is to provide a composition and method of treating keratins that can be easily incorporated into shampoos, conditioners and styling products.

Another object, feature, and/or advantage of the present invention is to provide a composition and method of treating keratins that repair and rebuild disulfide bonds.

These and/or other objects, features, and/or advantages of the present invention will be apparent to those skilled in the art. The present invention is not to be limited to or by these objects, features, and advantages. No single aspect need provide each and every object, feature, or advantage.

According to one aspect of the present invention, a composition for improving and protecting keratins is provided. The composition may comprise up to 60% olefinic compounds. In particular, the olefinic compounds may be comprised of 2-4 unactivated double bonds, the unactivated double bonds consisting of covalent bonds. The olefinic compounds may comprise fatty acid esters of polyhydric alcohols, unsaturated fatty acid amides, quaternized unsaturated fatty acid amides, fatty acid esters of monohydric alcohols, or combinations thereof. Notably, the composition for improving and protecting keratins does not comprise a Michael acceptor.

According to another aspect of the present invention a method for improving and protecting keratins is provided. The method may comprise providing keratins, such as hair, nails, skin, hooves, claws, feathers and/or horns. The method may further comprise providing the composition of the present invention as described above. The method may also comprise providing a chemical oxidative treatment. Chemical oxidative treatments utilized by the method of the present invention may include, but are not limited to, keratin bleaching, keratin coloring and/or keratin perming. Alternatively, the method may comprise providing a latent oxidative treatment. According to the method of the present invention the chemical or latent oxidative treatment may be applied directly to the keratins, wherein the composition of the present invention may be applied thereafter or simultaneously. The method of the present invention further comprises treating the keratins via the application of the chemical or latent oxidative treatment and the composition of the present invention to improve the overall health of the keratins, in particular texture, body, shine and strength.

Different aspects may meet different objects of the invention. Other objectives and advantages of this invention will be more apparent in the following detailed description taken in conjunction with the figures. The present invention is not to be limited by or to these objects or aspects.

DETAILED DESCRIPTION OF THE INVENTION

According to one aspect of the present invention, a composition for improving and protecting keratins is provided. The composition may comprise up to 60% olefinic compounds, preferably 0.5-55% olefinic compounds, activated or unactivated toward addition reaction across the double bond. In particular, the olefinic compounds may be comprised of at least one unactivated double bond, the at least one unactivated double bond solely consisting of covalent bonds. Alternatively, the olefinic compounds may have a plurality of unactivated double bonds, the unactivated double bonds solely consisting of covalent bonds. Still alternatively, the olefinic compounds may comprise 2-4 unactivated double bonds, the 2-4 unactivated double bonds solely consisting of covalent bonds. Notably, the composition of the present invention does not comprise a Michael acceptor.

The olefinic compounds of the composition of the present invention may comprise amide and ester derivatives of unsaturated fatty acids, wherein the hydrophobic fatty acid radical contains at least one isolated double bond that is not conjugated to another double bond, a carboxy group, or a carbonyl group. In particular, the composition of the present invention must include at least one olefinic compound comprising fatty acid esters of polyhydric alcohols, wherein suitable examples include, but are not limited to:

a) Di- and triglycerides (e.g., glycerol di- and trioleate), having the structures:

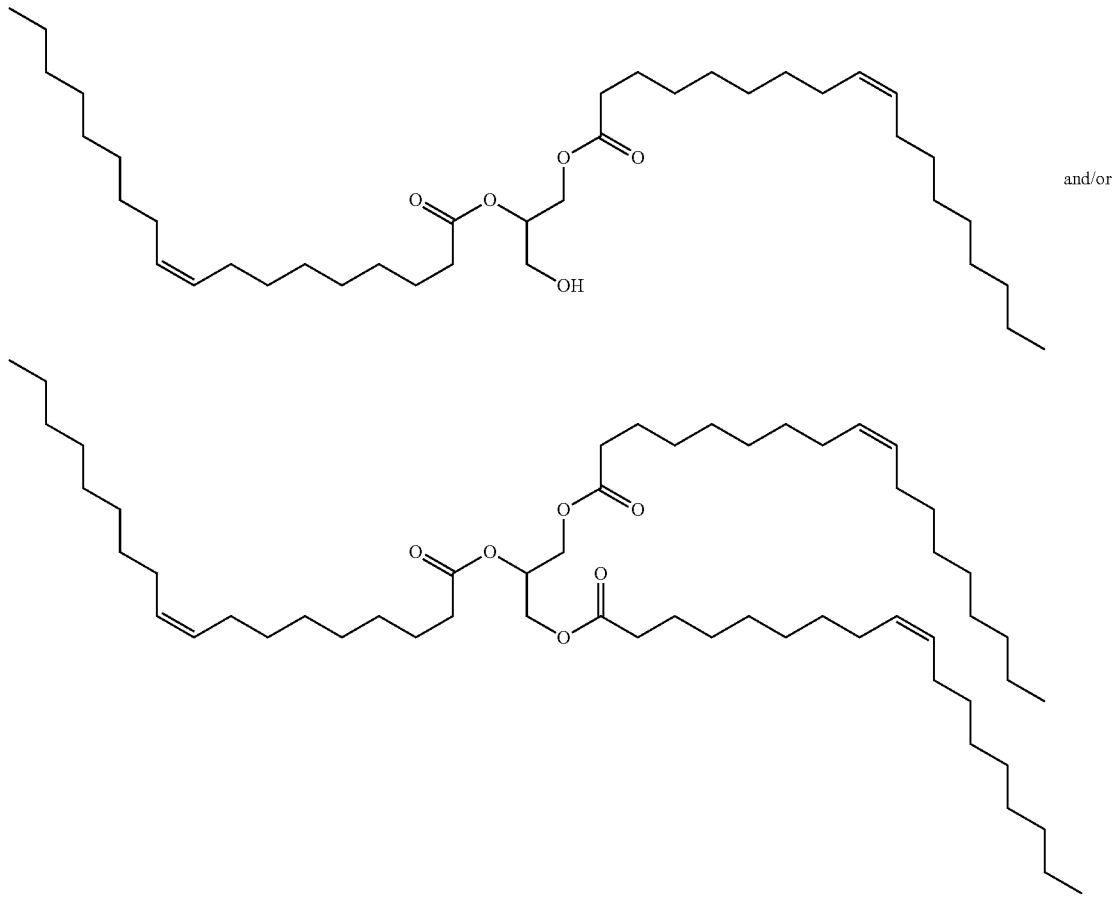

and/or b) Sorbitan Trioleate, having the structure:
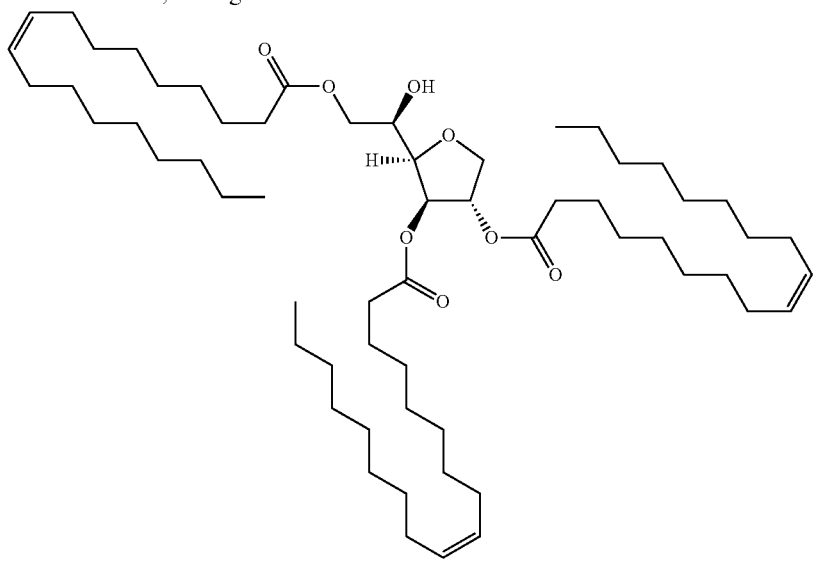
c) Sorbitan Sesquioleate, having the structure:
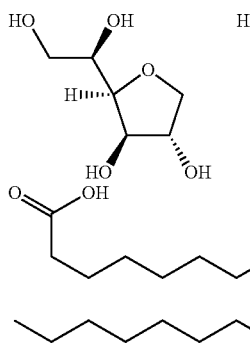
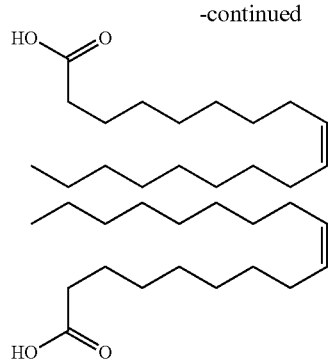
-continued
d) Polyoxyethylene Dioleate, having the structure:
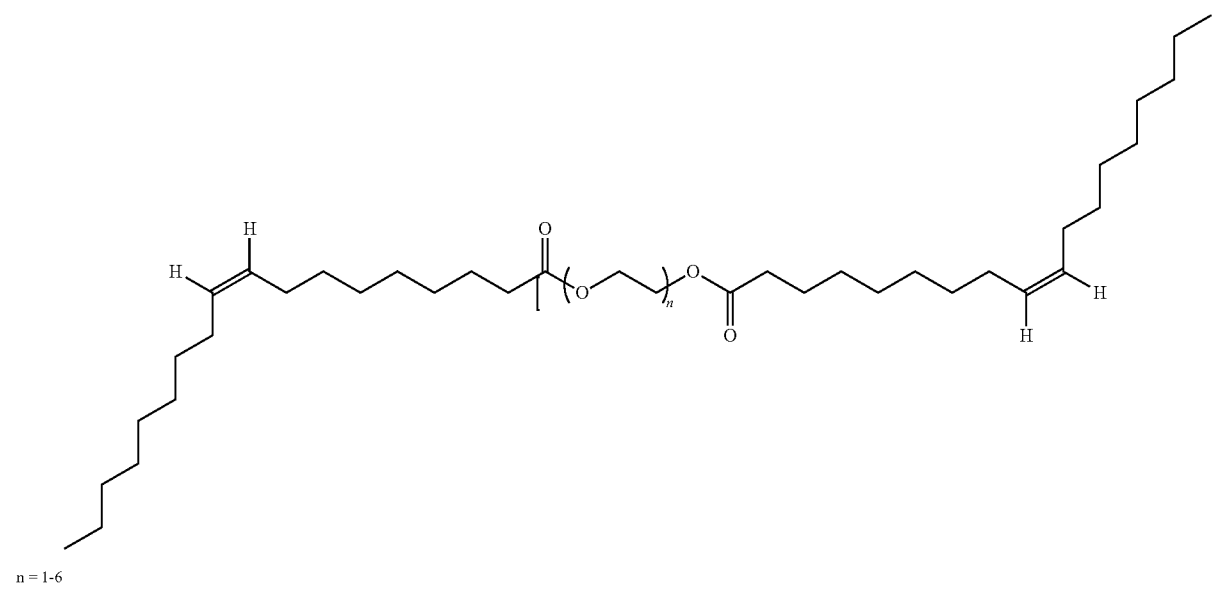
n = 1-6 e) Anhydrosorbitol Dioleate, having the structure:
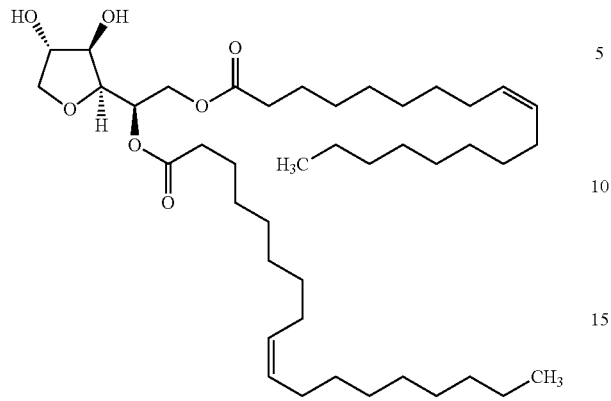
f) Sucrose Dioleate, having the structure:
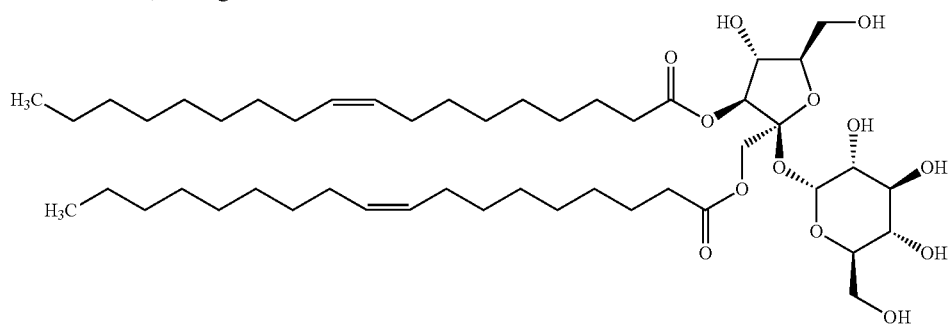
g) Methyl Glucose Dioleate and ethoxylated derivatives, having the structure:
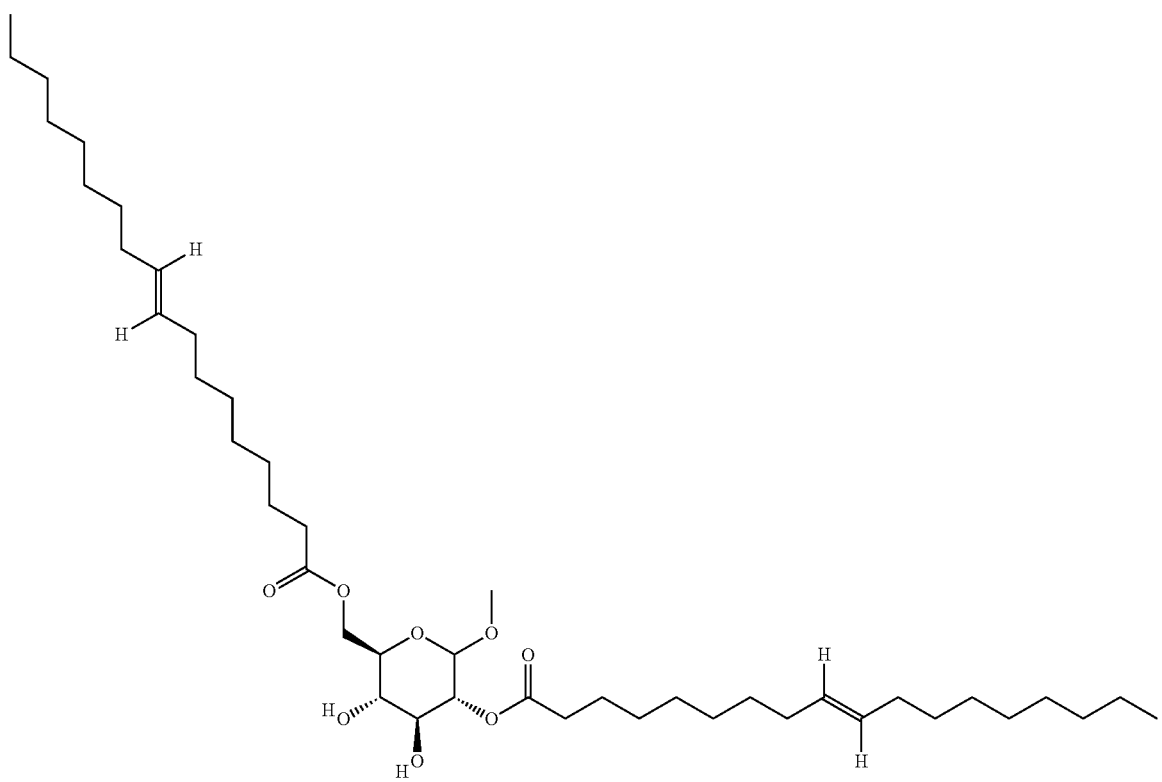

Additionally, the olefinic compounds of the composition of the present invention may comprise unsaturated fatty acid amides of the formula $R_1$—C(O)—$NR_2R_3$, wherein $R_1$ may comprise a $C_9$-$C_{22}$ fatty acid radical having at least one isolated double bond, and wherein $R_2$ and/or $R_3$ may comprise H or a $C_1$-$C_4$ alkyl or a $C_1$-$C_4$ hydroxyalkyl or higher alkoxylated analogs. Suitable examples of unsaturated fatty acide amides include, but are not limited to: Linoleamide MEA, DIPA, MIPA; Oleamide MEA, MIPA, DIPA; Soyamide MEA, DIPA, MIPA; and Cocamide MEA, DIPA, MIPA.

The olefinic compounds of the composition of the present invention may also comprise quaternized unsaturated fatty acid amides, having the structure:

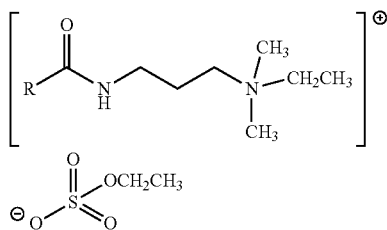

wherein R=unsaturated fatty acid or fatty acid fraction derived from whole-oil rich in unsaturated fatty acid. Suitable examples of quaternized unsaturated fatty acid amides include, but are not limited to: Soyamidopropyl Ethyldimonium Ethosulfate; Linoleamideopropyl Ethyldimonium Ethosulfate; and Oleamidopropyl Ethyldimonium Ethosulfate.

Furthermore, the olefinic compounds of the composition of the present invention may also comprise fatty acid esters of monohydric alcohols of the formula $R_1$—C(O)—$OR_2$, wherein $R_1$ may comprise a $C_9$-$C_{22}$ fatty acid radical having at least one isolated double bond, and wherein $R_2$ may comprise a $C_2$-$C_{22}$ alcohol, branched or unbranched, saturated or unsaturated. Notably, if both $R_1$ and $R_2$ are unsaturated the total number of double bonds in the molecule is preferably 2-4.

Compositions of the present invention as described above improve and protect the overall health of keratins when incorporated into a treatment regimen, including texture, body, shine and strength. The composition of the present invention may provide additional benefits to keratins such as improved elasticity, manageability, style retention, bounce, wet and dry combing, reduction of fizz and durability. The composition of the present invention may further seal down the cuticle of keratins, in particular hair, to protect the hair during and after chemical oxidative treatments. When the composition of the present invention is applied to keratins a more uniform result is obtained, for example, a more uniform color deposition may be achieved during hair coloring and a more uniform lift is achieved during hair bleaching. These beneficial effects are not only immediate-but durable as well-lasting through at least ten shampoos.

Another aspect of the present invention comprises a method for improving and protecting keratins. The method may comprise providing keratins, such as hair, nails, skin, hooves, claws, feathers and/or horns. As a non-limiting example, the method may comprise providing a head of human hair. The method may further comprise providing the composition of the present invention as described above. The method may also comprise providing a chemical oxidative treatment. A chemical oxidative treatment may utilize a peroxygen species to either directly or indirectly alter the color, tertiary structure or quaternary structure of keratin. Keratins possess a high sulfur content, which may exist as a free thiol group or in cross-links resulting from the oxidation of two proximal thiol groups to form a disulfide bond. Thiol radicals, known to add across alkenes, may be generated by oxidation.

In particular, the chemical oxidative treatment may comprise keratin bleaching, such as hair bleaching. Hair bleaching alters the hair's natural melanin derived pigmentation after applying hydrogen peroxide, peroxy salts and/or alkali compositions. For example, hair bleaching may include commercial hair bleaching kits or highlighters typically in the form of a powder containing a variety of peroxy salts such as sodium peroxycarbonate, or may otherwise exist in multi-component forms based on an anhydrous, semi-solid suspension of the peroxy salt mixed with a cream emulsion (cream bleach) or a micellar solution (oil bleach). Peroxy salts are known to those skilled in the art to be a solid source of hydrogen peroxide. When peroxy salts combine with water present in the hydrogen peroxide developer used with the commercial bleaching kit, the peroxy salts slowly dissolve and liberate hydrogen peroxide. Bleach is mixed with a hydrogen peroxide developer, according to the commercial bleach manufacturer's instructions, such that the initial concentration of hydrogen peroxide in the resulting bleach solution as applied to the hair ranges from 1-15%. Through slow dissolution of the peroxy salts and resulting formation of hydrogen peroxide, a steady state concentration of hydrogen peroxide is achieved over the course of 30-50 minutes to produce a high-lift result with very little damage to the hair. According to the method of the present invention the chemical oxidative treatment (e.g., hair bleaching) may be applied directly to the hair, wherein the composition of the present invention is applied thereafter. Alternatively, the composition of the present invention may be included as an additive in the chemical oxidative treatment (e.g., hair bleach) and applied to the hair simultaneously, wherein the resulting solution applied to the hair comprises up to 40% of the composition of the present invention.

Alternatively or in addition to, the chemical oxidative treatment may comprise keratin coloring, such as hair coloring. Hair coloring is the process wherein low molecular weight aromatic amines, aromatic phenols and aromatic aminophenols in the presence of an alkalizing agent and hydrogen peroxide diffuse into keratin and oxidatively couple to alter the natural color of the hair. Hair coloring utilized in the method of the present invention may comprise commercial products that include micellar solutions or emulsions containing aromatic amines, phenols, aminophenols or other aromatic oxidation intermediates known to those skilled in the art to undergo an oxidative coupling to produce color on and inside the shaft of the hair. Commercial hair color kits comprise a hair color base that may be mixed with a hydrogen peroxide-containing developer, according to the commercial hair color base manufacturer's instructions, such that the concentration of hydrogen peroxide in the resulting hair color solution as applied to the hair ranges from 1-15%. According to the method of the present invention the chemical oxidative treatment (e.g., hair coloring) may be applied directly to the hair, wherein the composition of the present invention is applied thereafter. Alternatively, the composition of the present invention may be included as an additive in the chemical oxidative treatment (e.g., hair color) and applied to the hair simultaneously, wherein the resulting solution applied to the hair comprises up to 40% of the composition of the present invention.

Alternatively or in addition to, the chemical oxidative treatment may comprise keratin perming, such as hair perming, wherein the hair perming process comprises two steps. In the first step of the perming process hair is mechanically stretched over curlers and chemically reduced to cleave native disulfide bonds. The reducing solution is rinsed from the hair after a set time as per the manufacturer's instructions. In the second step of the perming process, hair undergoes a subsequent oxidation using dilute hydrogen peroxide with the hair still curled on the perming rods to form new disulfide bonds. Thus, hair perming chemically alters the tertiary and quaternary structure of the keratin to achieve an altered curl pattern to the hair. According to the method of the present invention, the aforementioned composition of the present invention may be included as an additive during the second step of the perming process and applied to the hair simultaneously, or applied after the oxidizing solution has been rinsed from the hair. Alternatively, the composition of the present invention may be applied to the hair subsequent the chemical oxidative treatment.

According to the method of the present invention, treating the keratins via the application of the chemical oxidative treatment and the composition of the present invention improves the overall health of the keratins, in particular texture, body, shine and strength. Additional benefits to keratins include improved elasticity, manageability, style retention, bounce, wet and dry combing, reduction of frizz and durability. The method of the present invention may further seal down the cuticle of keratins, in particular hair, to protect the hair during and after the chemical oxidative treatments. When the method of the present invention is applied to keratins a more uniform result is obtained, for example, a more uniform color deposition may be achieved during hair coloring and a more uniform lift is achieved during hair bleaching. These beneficial effects are not only immediate-but durable as well-lasting through at least ten shampoos.

In yet another aspect of the present invention, a method for improving and protecting keratins is provided. The method may comprise providing keratins, such as hair, nails, skin, hooves, claws, feathers and/or horns. As a non-limiting example, the method may comprise providing a head of human hair. The method may further comprise providing the composition of the present invention as described above. The method may also comprise providing a latent oxidative treatment. According to the method of the present invention the latent oxidative treatment may be applied directly to the keratins, wherein the composition of the present invention is applied thereafter. Alternatively, the composition of the present invention may be included as an additive in the latent oxidative treatment and applied to the keratins simultaneously.

In particular, the latent oxidative treatment may comprise a pretreatment step of applying a dilute solution of hydrogen peroxide to the keratins, such as hair, the dilute solution ranging in concentration from 0.25-7.0% hydrogen peroxide. The hydrogen peroxide solution may be either rinsed-off or left-on the hair. Hair pretreated with the hydrogen peroxide solution may subsequently, or simultaneously, be treated with the composition of the present invention to improve the overall health of the hair. In particular, pretreatment of hair with the hydrogen peroxide solution can be used to generate thiyl radical residues in the keratin, which can be used to react with the olefinic compounds of the composition of the present invention by addition across the double bond, forming a carbon sulfur bond via a radical addition mechanism. The product of the radical addition is a new radical which is a conjugate of the keratin having the olefinic compound grafted to it. Through a second radical addition with another molecule of the olefinic compound, this new radical can be propagated, or the radical addition mechanism can be terminated by combining with another thiyl radical generating a second carbon sulfur bond between the grafted keratin and a proximal "native" domain on the keratin bearing a thiol group. Thus, a new infrastructure composed entirely of covalent bonds linking two proximal protein domains is created with respect to either the primary, secondary, tertiary or quaternary structure of the keratin. This infrastructure, much like a native disulfide bond provides strength and structural stability to the keratin. For these reasons, reacting the thiol group in the manner of the present invention repairs damage to broken disulfide bonds, reinforces the structure of the keratin and protects it from further damage.

Alternatively or in addition to, the latent oxidative treatment may comprise the compound of the present invention incorporated into convenient over the counter products such as shampoos, conditioners and styling products such as hair spray, serums, mousses, heat-styling sprays, pomades, etc. Consequently, the compound of the present invention may be pre-deposited on the keratin to promote an immediate beneficial effect whether from a rinse-off or leave-in application. In particular, the thiol-containing domains of the keratin and the residue of the olefinic compounds from the hair products described above remain in intimate contact wherein they may be exposed to radical chemical processes taking place within the environment (e.g., smog and ozone) or exposure to environmental conditions (e.g., air oxidation, ultraviolet light, visible light) wherein thiyl radical initiation may take place.

According to the method of the present invention, treating the keratins via the application of the latent oxidative treatments as described above and the composition of the present invention improves the overall health of the keratins, in particular texture, body, shine and strength. Additional benefits to keratins include improved elasticity, manageability, style retention, bounce, wet and dry combing, reduction of frizz and durability. The method of the present invention may further seal down the cuticle of keratins, in particular hair, to protect the hair during and after the chemical oxidative treatments. When the method of the present invention is applied to keratins a more uniform result is obtained, for example, a more uniform color deposition may be achieved during hair coloring and a more uniform lift is achieved during hair bleaching. These beneficial effects are not only immediate-but durable as well-lasting through at least ten shampoos.

While intended for humans, the composition and method of the present invention for improving and protecting keratins may be used for horses, cattle, llamas, alpacas, dogs, felines, birds and other creatures possessing keratin. Thus, the composition and method of the present invention for improving and protecting keratins may be incorporated into all manner of treatments to hair, nails, skin, hooves, claws, feathers and horns. Moreover, the composition and method of the present invention are universally applicable to be incorporated into shampoos, conditioners and styling products of all types and manufacturers. Although the invention is described and illustrated with respect to preferred aspects thereof, it is not to be so limited since changes and modifications may be made therein which are within the full intended scope of the invention.

EXAMPLES

Example 1

Comparison of Traditional Hair Bleaching with Additive versus Placebo

General.

A human female subject participated in testing, wherein the subject had bleached and colored her hair approximately one month prior to testing and the hair was of a medium damage level.

Traditional Hair Bleach.

SUPER STAR® 40 volume creamy developer (12% hydrogen peroxide in an oil-in water emulsion) and SUPER STAR® PRIME WHITE™ were utilized per the manufacturer's instructions.

Additive.

An additive comprising the composition of the present invention was provided, as follows:

| Components of Additive | Percentage of Additive |
| --- | --- |
| Water | 61.23% |
| PEG-120 methyl glucose dioleate | 5.00% |
| Methyl gluceth-10 | 5.00% |
| Dimethyl isosorbide | 2.00% |
| Methyl chloroisothiazolinone | 0.01% |
| Methylisothiazolinone | 0.01% |
| Bis-ethyl (isostearylimidazoline) isostearamide | 3.00% |
| Soyamidopropyl ethyldimonium ethosulfate | 3.75% |
| Sorbitan trioleate | 10.00% |
| Sorbitan sesquioleate | 10.00% |

Methods.

7.5 ml of the additive was prepared and thoroughly mixed with a freshly prepared hair bleaching mixture comprising 2 fluid ounces (60 ml) of SUPER STAR® 40 volume creamy developer (12% hydrogen peroxide in an oil-in water emulsion) and 30 grams of SUPER STAR® PRIME WHITE™ bleaching powder. The resulting additive/beach mixture was applied to ½ of the subject's head of hair. A placebo was applied to the other ½ of the subject's head of hair, wherein no additive was applied. The subject's entire head of hair was allowed to bleach for thirty minutes and then rinsed. Both sides of the subject's head of hair were shampooed with NATURE'S ADVANTAGE® Honey and Almond Shampoo, rinsed and conditioned with NATURE'S ADVANTAGE® Honey and Almond Conditioner. The subject's entire head of hair was then rinsed, combed, detangled and styled by brushing and blow drying.

Results.

Detangling was much easier on the ½ of the subject's head of hair wherein additive was applied. Moreover, the ½ of the subject's head of hair wherein additive was applied was easier to style, had more manageability, an improved shine and a soft silky feel with less comb-drag during dry combing as compared to the placebo. The ½ of the subject's head of hair wherein additive was applied had increased elasticity and style retention as compared to the other side of the subject's head of hair with the placebo. The lift to the original color was uniform across the subject's entire head of hair with the color going from a medium brown to a light golden blonde. The subject's entire head of hair was then colored as set forth in Example 2 (below), maintaining additive on the same side of the subject's head of hair as in the bleaching process of Example 1.

Example 2

Comparison of Traditional Hair Coloring with Additive Versus Placebo

General.

A human female subject participated in testing, wherein the subject had bleached and colored her hair approximately one month prior to testing and the hair was of a medium damage level.

Traditional Hair Color.

ION® COLOR BRILLIANCE™ 2N Demi Permanent Hair Color and ION® COLOR BRILLIANCE™ 20 volume creamy developer were utilized per the manufacturer's instructions.

Additive.

An additive comprising the composition of the present invention was provided, as follows:

| Components of Additive | Percentage of Additive |
| --- | --- |
| Water | 61.23% |
| PEG-120 methyl glucose dioleate | 5.00% |
| Methyl gluceth-10 | 5.00% |
| Dimethyl isosorbide | 2.00% |
| Methyl chloroisothiazolinone | 0.01% |
| Methylisothiazolinone | 0.01% |
| Bis-ethyl (isostearylimidazoline) isostearamide | 3.00% |
| Soyamidopropyl ethyldimonium ethosulfate | 3.75% |
| Sorbitan trioleate | 10.00% |
| Sorbitan sesquioleate | 10.00% |

Methods.

The additive was prepared and mixed with 2 fluid ounces of ION® COLOR BRILLIANCE™ 2N Demi Permanent Hair Color and 2 fluid ounces of ION® COLOR BRILLIANCE™ 20 volume creamy developer (6% hydrogen peroxide in an oil-in water emulsion). The additive was incorporated at a rate of 3.75 ml to a total of 120 ml of the traditional hair color solution, mixed in completely, and was applied to ½ of the subject's head of hair. A placebo was applied to the other ½ of the subject's head of hair, wherein no additive was applied. The color was allowed to develop for twenty minutes and then rinsed, combed, detangled and styled by brushing and blow drying.

Results.

Detangling was much easier on the ½ of the subject's head of hair wherein additive was applied. Moreover, the subject's hair with additive applied was easier to style, had more manageability, an improved shine and a soft silky feel with less comb-drag during dry combing as compared to the other side of the subject's head of hair with the placebo. The hair with additive applied had increased elasticity and style retention as compared to the placebo. The test subject was requested to come back in two weeks after five shampooing's. After two weeks, the manageability, shine, body and soft silky feel remained noticeable on the ½ of the subject's head of hair wherein additive had been applied.

What is claimed is:

1. A method for improving and protecting keratins, the method comprising:
providing keratins, the keratins comprising at least one thiol group;
providing a keratin treatment composition, comprising:
a) 0.1-5% by weight olefinic compounds comprising unsaturated fatty acid esters of polyhydric alcohols, wherein the unsaturated fatty acid esters of polyhydric alcohols is selected from the group consisting of the structures:

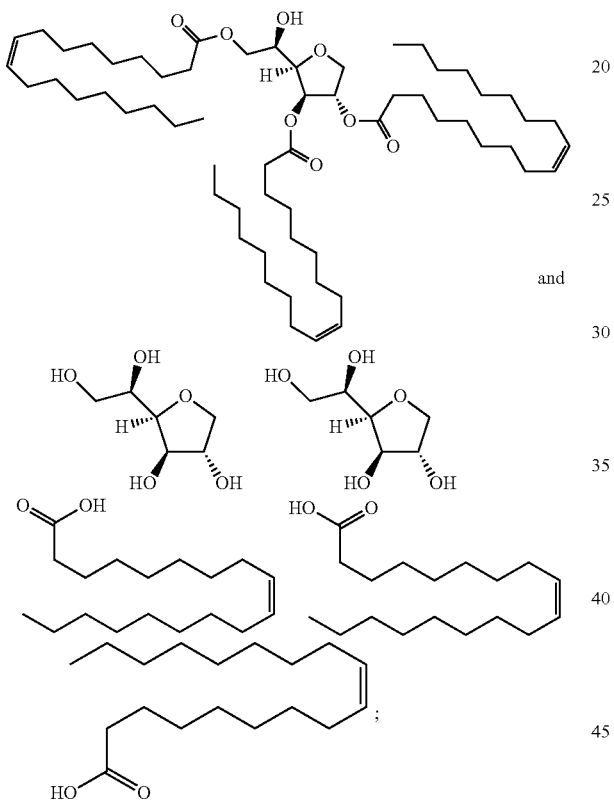

b) 0.1-60% by weight olefinic compounds comprising:
i. unsaturated fatty acid amides of the formula $R_1$—C(O)—$NR_2R_3$, wherein $R_1$ is a $C_9$-$C_{22}$ fatty acid radical having at least one isolated double bond, and wherein $R_2$ and/or $R_3$ is H or a $C_1$-$C_4$ alkyl or a $C_1$-$C_4$ hydroxyalkyl or higher alkoxylated analogs;
ii. quaternized unsaturated fatty acid amides, having the

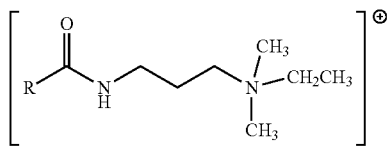

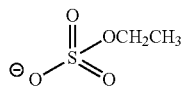

structure:
wherein R=unsaturated fatty acid or fatty acid fraction derived from whole-oil rich in unsaturated fatty acid;
iii. fatty acid esters of monohydric alcohols of the formula $R_1$—C(O)—$OR_2$, wherein $R_1$ is a $C_9$-$C_{22}$ fatty acid radical having at least one isolated double bond, and wherein $R_2$ is a $C_2$-$C_{22}$ alcohol; and
iv. mixtures thereof;
c) the olefinic compounds comprising at least one unactivated double bond;
d) the at least one unactivated double bond consisting of a covalent bond; and
e) the keratin treatment composition does not comprise a Michael acceptor;
providing a chemical oxidative treatment;
applying the chemical oxidative treatment to the keratins;
generating thiyl radicals in the keratin via the chemical oxidative treatment;
applying the keratin treatment composition to the keratins;
creating a thiol-ene reaction between the thiyl radicals in the keratin and the at least one unactivated double bond of the olefinic compounds;
modifying the at least one thiol group in the keratins through the thiol-ene reaction; and
forming a carbon-sulfur bond between the keratins and the at least one unactivated double bond of the olefinic compounds;
wherein the formation of the carbon-sulfur bond between the keratins and the at least one unactivated double bond of the olefinic compounds provides permanent conditioning to improve the overall health of the keratins.

2. The method for improving and protecting keratins of claim 1, wherein the keratins are hair, nails, skin and/or combinations thereof.

3. The method for improving and protecting keratins of claim 2, wherein the overall health of the keratins comprises texture, body, shine and strength.

4. The method for improving and protecting keratins of claim 3, wherein the chemical oxidative treatment comprises hair bleaching.

5. The method for improving and protecting keratins of claim 3, wherein the chemical oxidative treatment comprises hair coloring.

6. The method for improving and protecting keratins of claim 3, wherein the chemical oxidative treatment comprises a neutralization step in hair perming.

7. The method for improving and protecting keratins of claim 3, wherein the keratin treatment composition is incorporated as an additive into the chemical oxidative treatment.

8. The method for improving and protecting keratins of claim 3, further comprising sealing cuticles of the keratins via the chemical oxidative treatment and the keratin treatment composition to protect the keratins.

9. The method for improving and protecting keratins of claim 3, wherein the at least one unactivated double bond is 2-4 unactivated double bonds, the 2-4 unactivated double bonds consisting of covalent bonds.

10. A method for improving and protecting keratins, the method comprising:
  providing keratins, the keratins comprising at least one thiol group;
  providing a keratin treatment composition, comprising:
    a) 0.1-5% by weight olefinic compounds comprising unsaturated fatty acid esters of polyhydric alcohols, wherein the unsaturated fatty acid esters of polyhydric alcohols is selected from the group consisting of the structures:

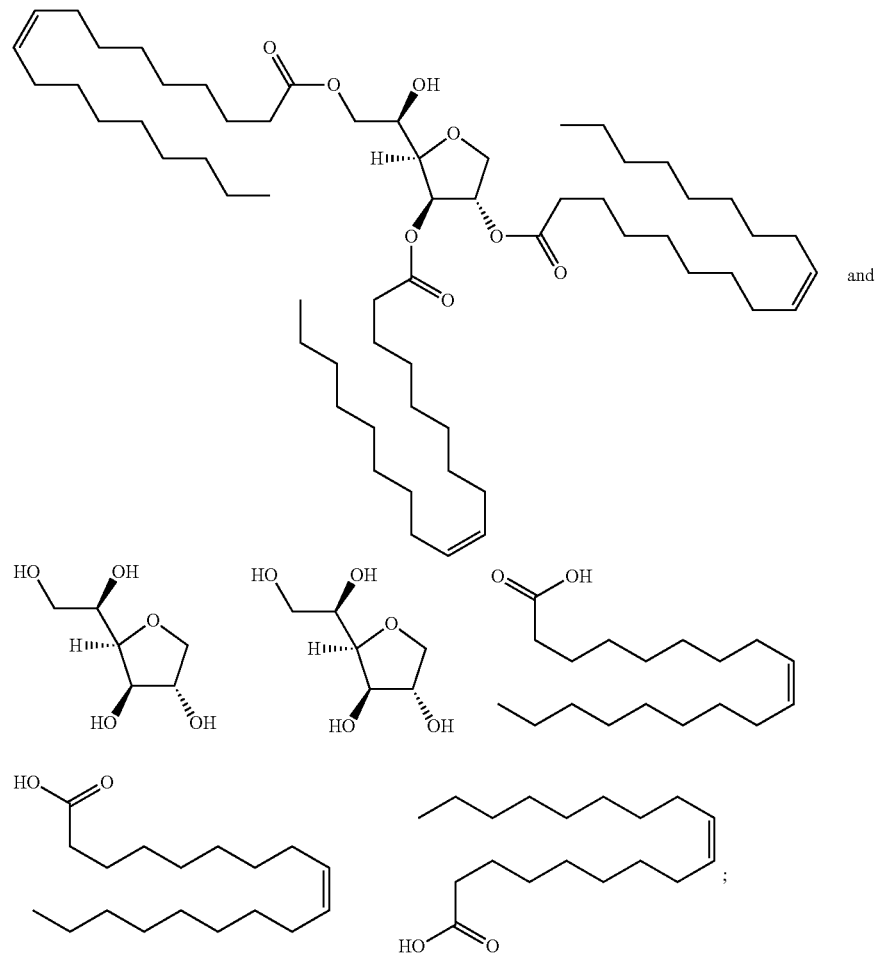

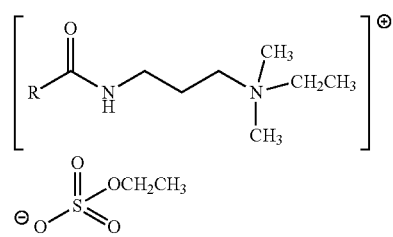

structure:
  wherein R=unsaturated fatty acid or fatty acid fraction derived from whole-oil rich in unsaturated fatty acid;
  iii. fatty acid esters of monohydric alcohols of the formula $R_1$—C(O)—$OR_2$, wherein $R_1$ is a $C_9$-$C_{22}$ b) 0.1-60% by weight olefinic compounds comprising:
      i. unsaturated fatty acid amides of the formula $R_1$—C(O)—$NR_2R_3$, wherein $R_1$ is a $C_9C_{22}$ fatty acid radical having at least one isolated double bond, and wherein $R_2$ and/or $R_3$ is H or a $C_1$-$C_4$ alkyl or a $C_1$-$C_4$ hydroxyalkyl or higher alkoxylated analogs;
      ii. quaternized unsaturated fatty acid amides, having the fatty acid radical having at least one isolated double bond, and wherein $R_2$ is a $C_2$-$C_{22}$ alcohol; and
      iv. mixtures thereof;
    b) the olefinic compounds comprising a plurality of unactivated double bonds;
    c) the plurality of unactivated double bonds consisting of covalent bonds; and e) the keratin treatment composition does not comprise a Michael acceptor;
providing a latent oxidative treatment;
applying the latent oxidative treatment to the keratins;
generating thiyl radicals in the keratin via the latent oxidative treatment;
applying the keratin treatment composition to the keratins;
creating a thiol-ene reaction between the thiyl radicals in the keratin and the plurality of unactivated double bonds of the olefinic compounds;
modifying the at least one thiol group in the keratins through the thiol-ene reaction; and
forming a carbon-sulfur bond between the keratins and the plurality of unactivated double bonds of the olefinic compounds;
wherein the formation of the carbon-sulfur bond between the keratins and the plurality of unactivated double bonds of the olefinic compounds provides permanent conditioning to improve the overall health of the keratins.

11. The method for improving and protecting keratins of claim 10, wherein the keratins are hair, nails, skin and/or combinations thereof.

12. The method for improving and protecting keratins of claim 11, wherein the overall health of the keratins comprises texture, body, shine and strength.

13. The method for improving and protecting keratins of claim 12, wherein the latent oxidative treatment comprises shampoos, conditioners and/or styling products.

14. The method for improving and protecting keratins of claim 13, wherein the plurality of unactivated double bonds is 2-4 unactivated double bonds, the 2-4 unactivated double bonds consisting of covalent bonds.

15. A method for improving and protecting keratins, the method comprising:
providing keratins, the keratins comprising at least one thiol group;
providing a keratin treatment composition, comprising:
a) 0.1-5% by weight olefinic compounds selected from the group consisting of the structures:

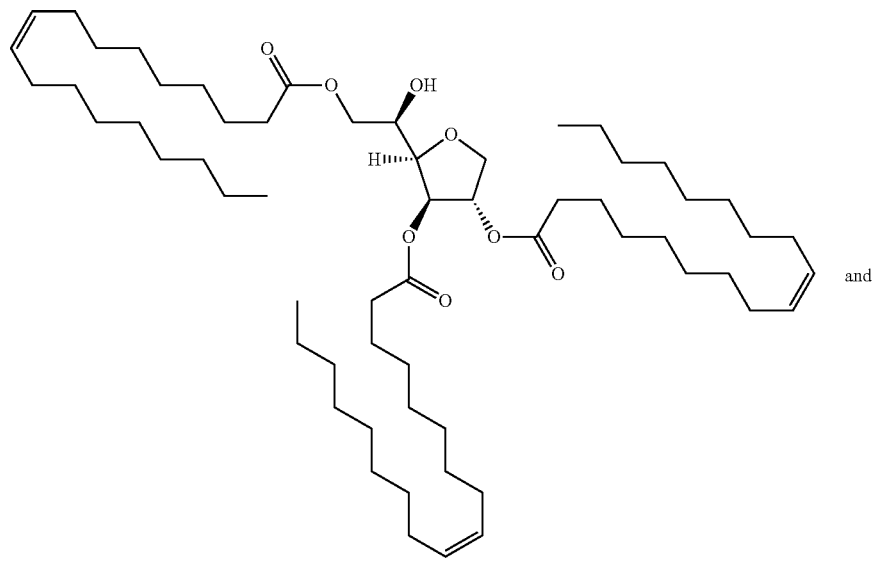

and

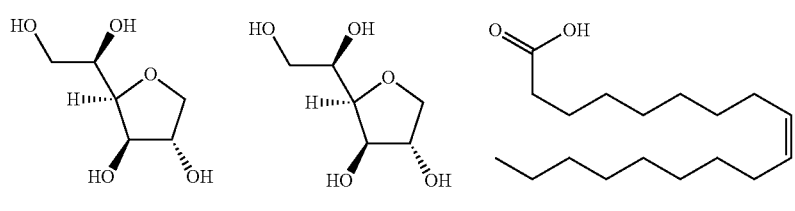

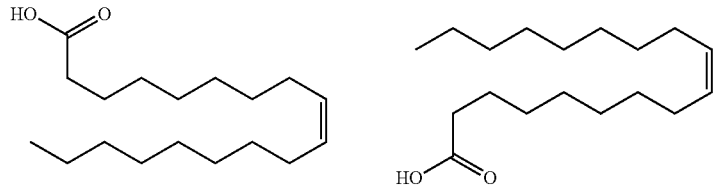

b) 0.1-60% by weight olefinic compounds selected from the group consisting of:
   i. unsaturated fatty acid amides of the formula $R_1$—C(O)—$NR_2R_3$, wherein $R_1$ is a $C_9$-$C_{22}$ fatty acid radical having at least one isolated double bond, and wherein $R_2$ and/or $R_3$ is H or a $C_1$-$C_4$ alkyl or a $C_1$-$C_4$ hydroxyalkyl or higher alkoxylated analogs;
   ii. quaternized unsaturated fatty acid amides, having the

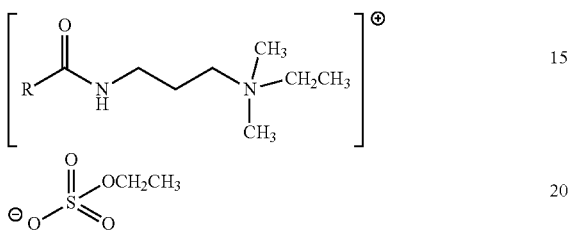

structure:
   wherein R=unsaturated fatty acid or fatty acid fraction derived from whole-oil rich in unsaturated fatty acid;
   iii. fatty acid esters of monohydric alcohols of the formula $R_1$—C(O)—$OR_2$, wherein $R_1$ is a $C_9$-$C_{22}$ fatty acid radical having at least one isolated double bond, and wherein $R_2$ is a $C_2$-$C_{22}$ alcohol; and
   iv. mixtures thereof;
c) the olefinic compounds comprising 2-4 unactivated double bonds;
d) the 2-4 unactivated double bonds consisting of covalent bonds; and
e) the keratin treatment composition does not comprise a Michael acceptor;
providing an oxidative treatment;
applying the oxidative treatment to the keratins;
generating thiyl radicals in the keratin via the oxidative treatment;
applying the keratin treatment composition to the keratins;
creating a thiol-ene reaction between the thiyl radicals in the keratin and the 2-4 unactivated double bonds of the olefinic compounds;
modifying the at least one thiol group in the keratins through the thiol-ene reaction; and
forming a carbon-sulfur bond between the keratins and the 2-4 unactivated double bonds of the olefinic compounds;
wherein the formation of the carbon-sulfur bond between the keratins and the 2-4 unactivated double bonds of the olefinic compounds provides permanent conditioning to improve the overall health of the keratins.

16. The method for improving and protecting keratins of claim 15, wherein the oxidative treatment is a chemical oxidative treatment comprising hair bleaching, hair coloring, a neutralization step in hair perming, and/or combinations thereof.

17. The method for improving and protecting keratins of claim 16, wherein the keratin treatment composition is incorporated as an additive into the chemical oxidative treatment.

18. The method for improving and protecting keratins of claim 15, wherein the oxidative treatment is a latent oxidative treatment comprising shampoos, conditioners and/or styling products.

* * * * *